United States Patent [19]

Klohs et al.

[11] Patent Number: 5,767,110
[45] Date of Patent: Jun. 16, 1998

[54] COMBINATION CHEMOTHERAPY

[75] Inventors: Wayne Daniel Klohs; Charles Dale Kowal, both of Ann Arbor, Mich.

[73] Assignee: Warner-Lambert Company, Morris Plains, N.J.

[21] Appl. No.: 763,601

[22] Filed: Dec. 11, 1996

Related U.S. Application Data

[62] Division of Ser. No. 359,488, Dec. 20, 1994, Pat. No. 5,597,830.

[51] Int. Cl.$^6$ .......... A61K 31/66; A61K 31/56; A61K 31/185; A61K 31/17
[52] U.S. Cl. .......... 514/119; 514/171; 514/553; 514/597
[58] Field of Search .......... 514/597, 119, 514/553, 171

[56] References Cited

U.S. PATENT DOCUMENTS

| | | | |
|---|---|---|---|
| 5,158,940 | 10/1992 | LaRocca et al. | 514/54 |
| 5,385,936 | 1/1995 | Flack et al. | 514/548 |

OTHER PUBLICATIONS

Studies of Suramin (Antrypol: Bayer 205), vol. 40, 1946, Dewey et al., pp. 119–124.
Journal of Clinical Oncology, vol. 7, No. 4, 1989, Stein et al., pp. 499–508.
Journal of the National Cancer Institute, vol. 86, No. 20, 1994, Chou et al., pp. 1517–1524.
Synergism and Antagonism in Chemotherapy, Chapter 6, 1991, Chou et al., pp. 223–241.
Journal of the National Cancer Institute, vol. 82, No. 14, 1990, Fruehauf et al., pp. 1206–1209.
Proceedings of the American Association for Cancer Research, vol. 35, 1994, Rago et al., p. 329, abstract 1956.
Molecular Pharmacology, vol. 33, No. 4, 1988, Zamora et al., pp. 454–462.
Carter et al, Chemotherapy of Lawler, 2nd ed, John Wiley & Sons, N.Y., N.Y., 1981 p. 126.

Primary Examiner—Jerome D. Goldberg
Attorney, Agent, or Firm—Charles W. Ashbrook

[57] ABSTRACT

Suramin in combination with a vinca alkaloid or estramustine is synergistic for treating cancer.

9 Claims, 6 Drawing Sheets

COMBINATION CHEMOTHERAPY

This is a divisional of U.S. application Ser. No. 08/359,488 filed Dec. 20, 1994, now U.S. Pat. No. 5,597,830.

BACKGROUND OF THE INVENTION

The invention concerns a method for treating tumors utilizing a combination of known oncolytic agents. The use of the agents together provides unexpectedly greater efficacy than employing the single agents alone.

Cancer chemotherapy has advanced dramatically in recent years. Many tumors can be effectively treated and irradicated utilizing compounds which are either naturally occurring products or synthetic agents. Cancer chemotherapy often entails use of a combination of agents, generally as a means of reducing the toxic effects that are often encountered with the individual agents when used alone.

We have now discovered a unique combination of known oncolytic agents which exhibit a dramatic synergistic effect. The combination utilizes the agent suramin, together with either a vinca alkaloid or estramustine. The combination is especially effective in treating both prostate and breast cancer.

Suramin is the hexasodium salt of a polysulfonated naphthylurea, namely 8,8'-[carbonylbis[imino-3,1-phenylenecarbonylimino(4-methyl-3,1-phenylene)carbonyl-imine]]bis-1,3,5-naphthalenetrisulfonic acid. It also is known as Germanin, Belgenyl, Maphuride, and Antrypol, hexasodium salt. Suramin has been utilized clinically since the 1920s as an antiparasitic agent, and more recently has been shown to be active in the treatment of metastatic cancer; Stein, et al., *J. Clin. Oncology* 1989;7(4):499–508. Fruehauf, et al., reported that the antitumor activity of suramin is potentiated by doxorubicin, especially against human prostate cell line PC-3; *J. Nat. Can. Inst.* 1990;82(14):1206–9. Suramin is known to have several toxic effects in some patients, including adrenal insufficiency, neuropathy, coagulopathy, hypocalcemia, and neurotoxic effects. Occurrence of these adverse effects often requires limiting the dose of suramin, or withdrawing treatment completely.

Several vinca alkaloids are commercially utilized to treat certain cancers. Vinblastine, for example, is an alkaloid isolated from *Vinca rosa*. Vinblastine sulfate is utilized clinically to treat Hodgkin's disease, lymphocytic lymphoma, histiocytic lymphoma, and breast cancer. Vincristine is another antitumor alkaloid isolated from *Vinca rosa*. Vindesine is a synthetic derivative of vinblastine These and other vinca alkaloids are known to have a variety of antineoplastic activities.

Estramustine is an estradiol derivative, namely estradiol 3-bis(2-chloroethyl)carbamate. It is utilized commercially as the phosphate sodium salt, and is indicated in the palliative treatment of patients with metastatic and/or progressive carcinoma of the prostate.

An object of this invention to provide a method for treating cancers, especially prostate cancer and breast cancer, with a combination comprising suramin together with either a vinca alkaloid or estramustine. A further object is to provide a composition comprising suramin and either a vinca alkaloid or estramustine.

SUMMARY OF THE INVENTION

This invention relates to a synergistic combination of antineoplastic agents, and to a method for treating tumors comprising administering the combination. The invention more particularly provides a composition comprising, as a first component, suramin, preferably as the hexasodium salt, and as a second component either a vinca alkaloid or estramustine.

The compositions of this invention consist essentially of the above active ingredients, or suitable salts thereof, together with common excipients, diluents, and carriers.

A preferred composition comprises suramin sodium (the hexasodium salt), together with vinblastine sulfate. Another preferred composition comprises suramin sodium together with estramustine phosphate sodium.

In a further embodiment of the invention, we provide a method for treating cancer comprising administering to an animal in need of treatment an effective amount of a combination of suramin and either a vinca alkaloid or estramustine.

A preferred method embraces treatment of prostate cancer and breast cancer.

A further preferred method employs an antitumor amount of suramin sodium and an effective amount of vinblastine sulfate.

Another preferred method employs an antitumor amount of suramin sodium and an antitumor amount of estramustine phosphate sodium.

DETAILED DESCRIPTION OF THE INVENTION

The compounds to be utilized in the method of this invention will be administered in doses commonly employed clinically. Suramin will be administered, for example, at doses from about 275 mg/m$^2$ to about 1000 mg/M$^2$, preferably from about 350 mg/m$^2$ to about 600 mg/m$^2$. Ideally, suramin will be administered at a dose which will produce plasma levels of about 100 to about 300 µg/mL. Suramin typically is administered by intravenous infusion over a 12- to 16-week period, as needed to maintain the indicated plasma levels. Suramin will be administered at about the same dose levels and frequency according to this invention.

The vinca alkaloid antitumor agents are generally administered by IV injection at doses of about 2 mg/m$^2$ to about 20 mg/m$^2$, generally about once each week during a treatment cycle of about 12 to 16 weeks. For example, vinblastine sulfate generally is administered to adults at a dose of about 3 to about 4 mg/m$^2$ in Week 1 of treatment. Doses generally are increased, for example, to about 5.5 mg/m$^2$ in Week 2, about 7.4 mg/m$^2$ in Week 3, about 9 mg/m$^2$ in Week 4, and about 1 mg/m$^2$ in Week 5 and thereafter during the course of treatment.

Estramustine generally is utilized clinically as the phosphate sodium salt. It usually is administered orally at a daily dose of about 10 to about 20 mg per kilogram of body weight. The doses often are given as 3 to 4 divided doses over a 12- to 16-hour period. According to this invention, estramustine will be administered at a dose of about 10 to about 20 mg/kg of animal body weight.

The combination of suramin with either a vinca alkaloid or estramustine has been found to have an unusually greater effect than expected. The combination exhibits a much greater than additive effect.

The combination provided by this invention has been evaluated in several assay systems, and the data has been analyzed utilizing a standard program for quantifying synergism, additivism, and antagonism among anticancer agents. The program is that described by Chou and Talalay, in "New Avenues in Developmental Cancer Chemotherapy" *Academic Press,* 1987, Chapter 2.

The method is based on the median-effect principle of the mass-action law using an enzyme kinetic system as a model. The equation is simple and describes the relationships between dose and effect regardless of the shape of the dose-effect curve. Two basic equations constitute the pillars of this methodology. To relate dose and effect for a single drug in the simplest way possible, the median-effect equation derived by Chou is given by:

$$f_a/f_u = (D/D_m)^m$$

or $$D = D_m [f_a/(1-f_a)]^{1/m}$$

where the right side represents the dose and the left side represents the effect, in which $f_a$ and $f_u$ are the fractions affected and unaffected, respectively, D is the dose, $D_m$ is the median-effect dose signifying the potency, and m is a coefficient signifying the shape of the dose-effect curve. From this equation Chou and Talalay derived the general equation for 2 or more drugs:

$$\left[\frac{(f_a)_{1,2}}{(f_u)_{1,2}}\right]^{1/m} = \left[\frac{(f_a)_1}{(f_u)_1}\right]^{1/m} + \left[\frac{(f_a)_2}{(f_u)_2}\right]^{1/m}$$

$$= +\alpha\left[\frac{(f_a)_1(f_a)_2}{(f_u)_1(f_u)_2}\right]^{1/m}$$

$$= \frac{(D)_1}{(D_m)_1} + \frac{(D)_2}{(D_m)_2} = \frac{\alpha(D)_1(D)_2}{(D_m)_1(D_m)_2}$$

where m=1 is for first-order Michaelis-Menten-type kinetics and m>1 (or m<1) is for higher order (or lower order) Hill-type kinetics. When alpha=0, the third term on the right side disappears and when alpha=1, the third term is conserved. Alpha=0 is used for mutually exclusive drugs and alpha=1 is used for mutually nonexclusive drugs. For drugs that have the same or similar modes of action, the effects of both drugs are mutually exclusive. For drugs that have different modes of action or act independently, the effects of both drugs are mutually nonexclusive. Since we do not know the mechanism of action of suramin, we analyze our data by both parameters.

A plot of fraction affected ($F_a$) versus combination index (CI) is called the $F_a$-CI plot. This plot indicates synergism, additivity, or antagonism of 2 drugs at various effect levels in a mixture that is serially diluted. If several mixtures are made, it is possible to estimate the optimal combination ratio for maximal synergy. Different effect levels usually give different degress of synergism, additivism, or antagonism. CI values <1 indicate synergism; CI values >1 indicate antagonism, and CI values that are 1 or hover around 1 indicate additivity. For anticancer agents, synergism at high effect levels ($F_a$) is clinically more relevant than synergism at low $F_a$ levels.

BRIEF DESCRIPTION OF DRAWINGS

In human prostate cancer PC-3 cells, analysis of the combination of suramin and vinblastine using $F_a$-CI plots demonstrates synergism at the higher $F_a$ values (FIG. 1). The combination of suramin plus estramustine (Emcyt) appears to be additive by the same analysis (FIG. 2). In contrast, a suramin-taxol combination is antagonistic against PC-3 cells (FIG. 3).

In human breast cancer MCF-7 cells, analysis of the combination of suramin and vinblastine using $F_a$-CI plots also demonstrates very strong synergism at all concentrations of both drugs (FIG. 4) The combination of suramin and estramustine is also synergistic at the highest effect concentrations (FIG. 5). As in PC-3 cells, the combination of suramin and taxol showed strong antagonism against MCF-7 cells (FIG. 6).

Figure 1:
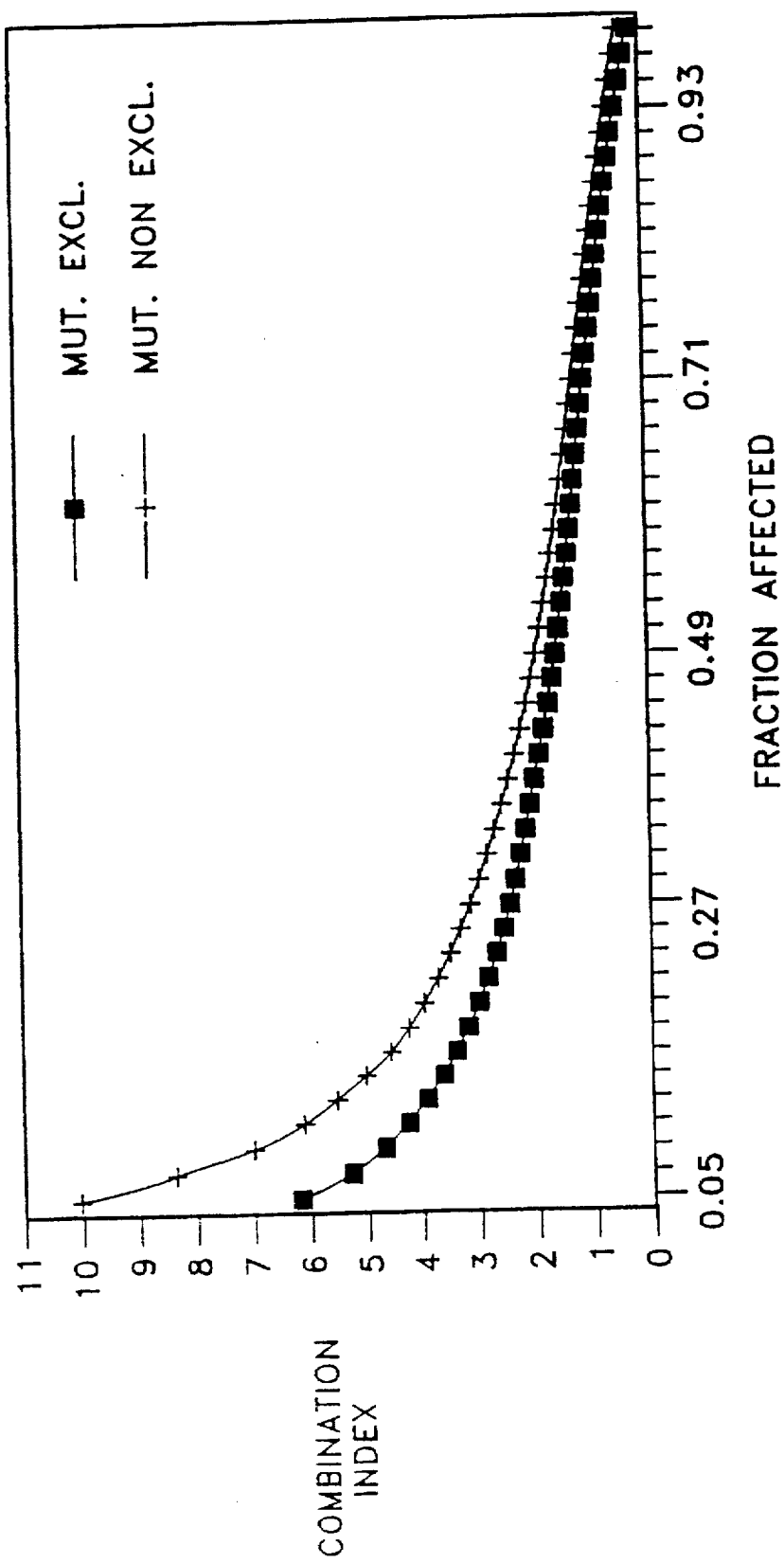
Figure 2:
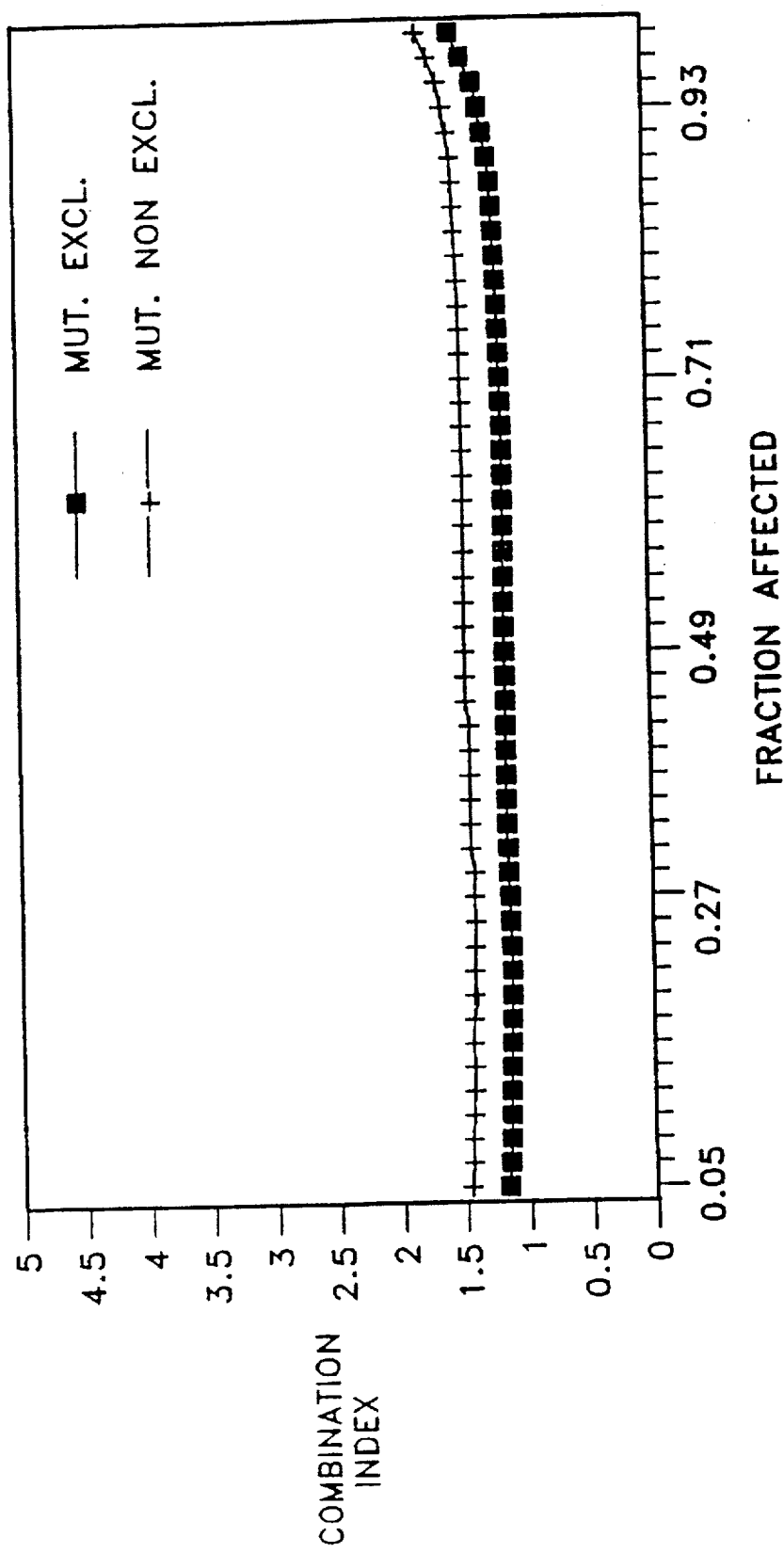
Figure 3:
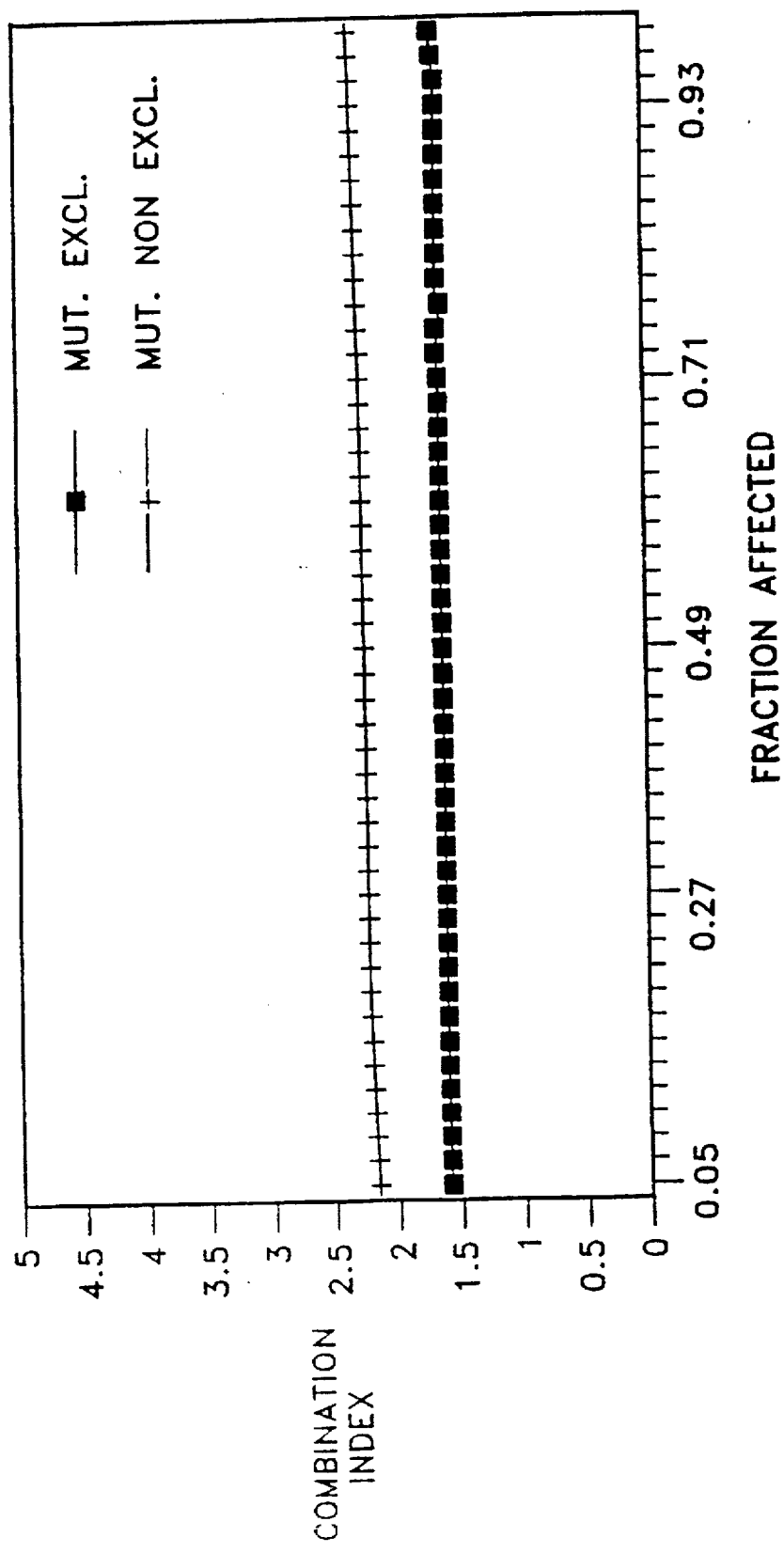
Figure 4:
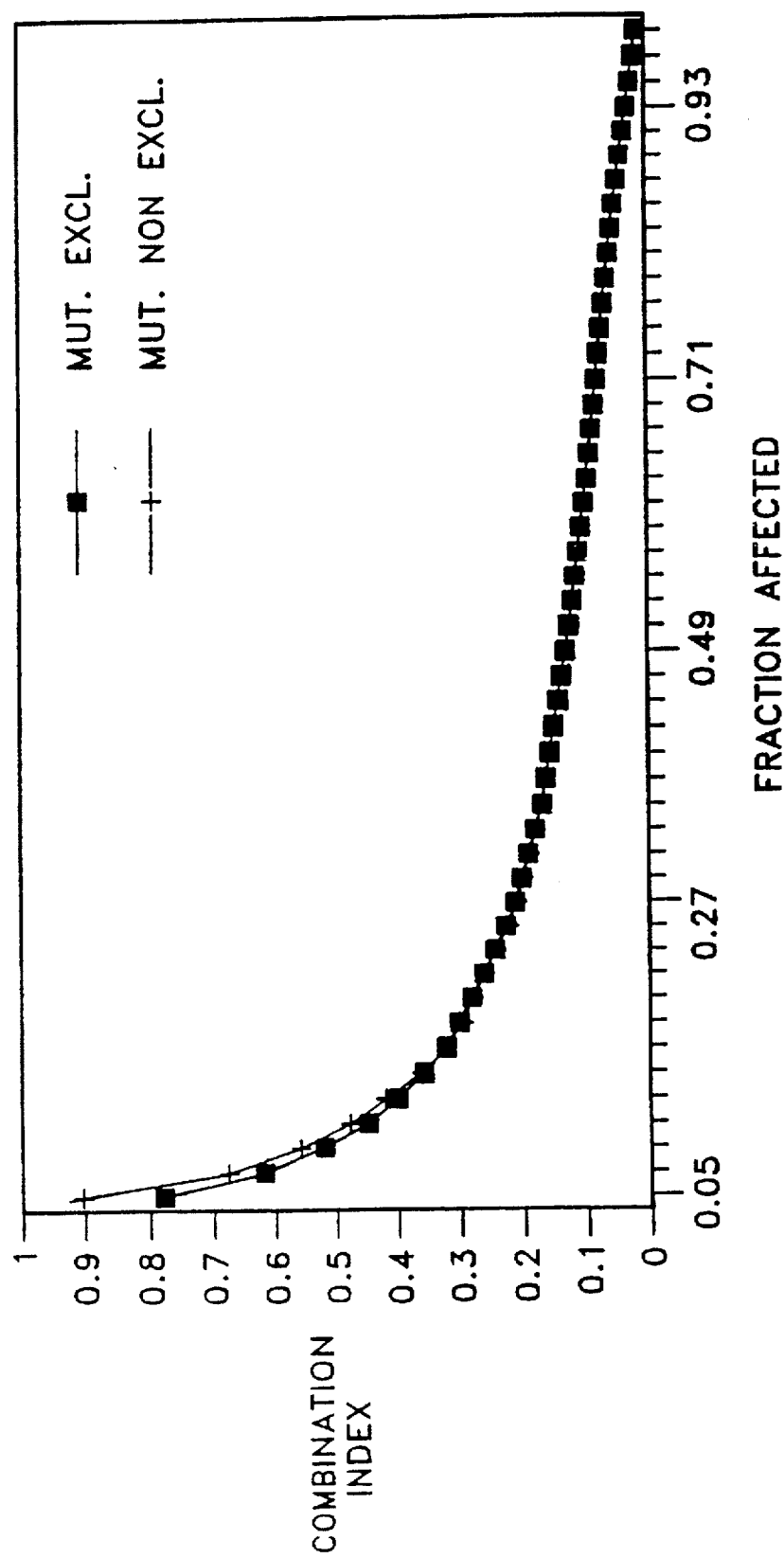
Figure 5:
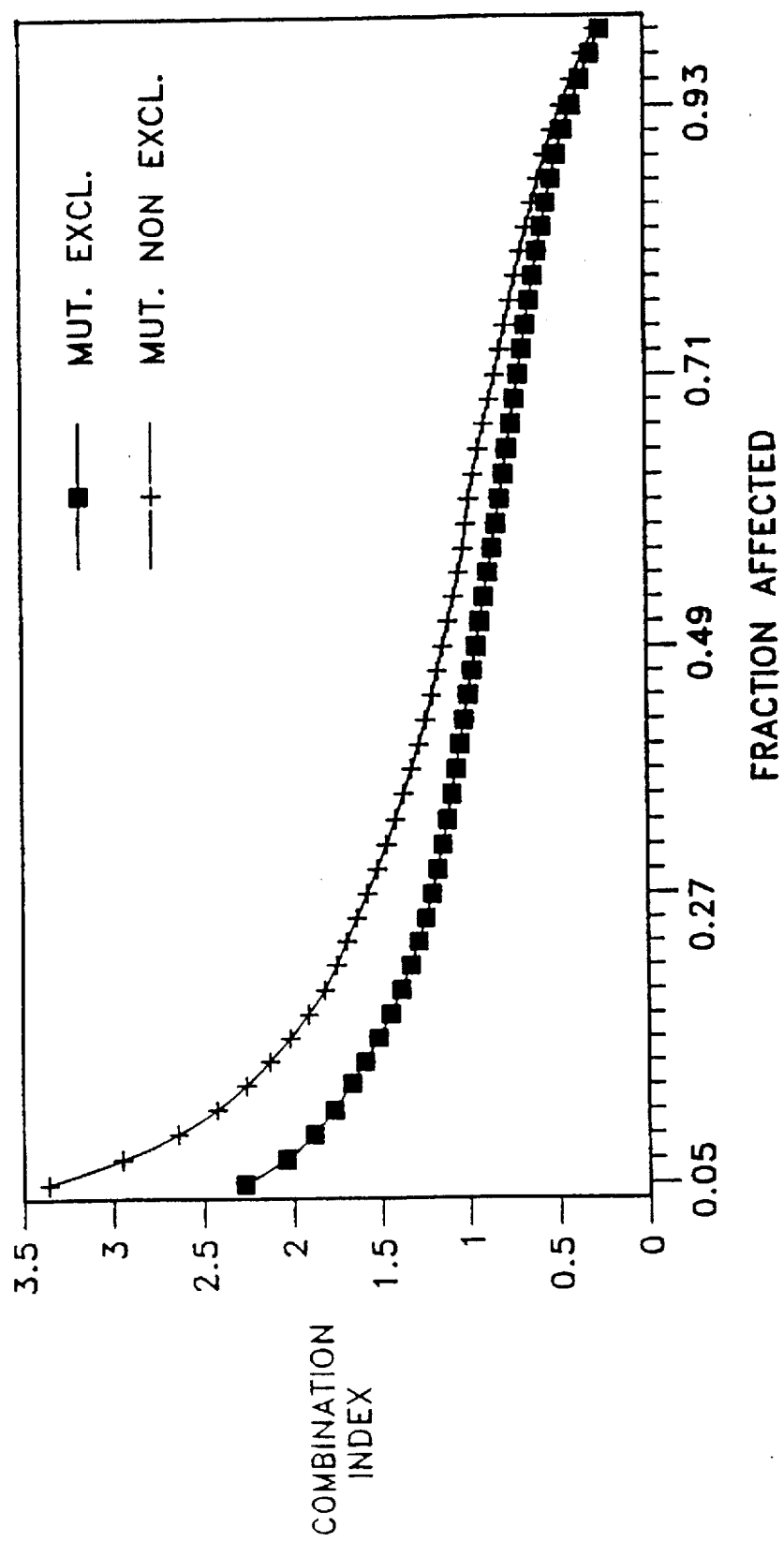
Figure 6:
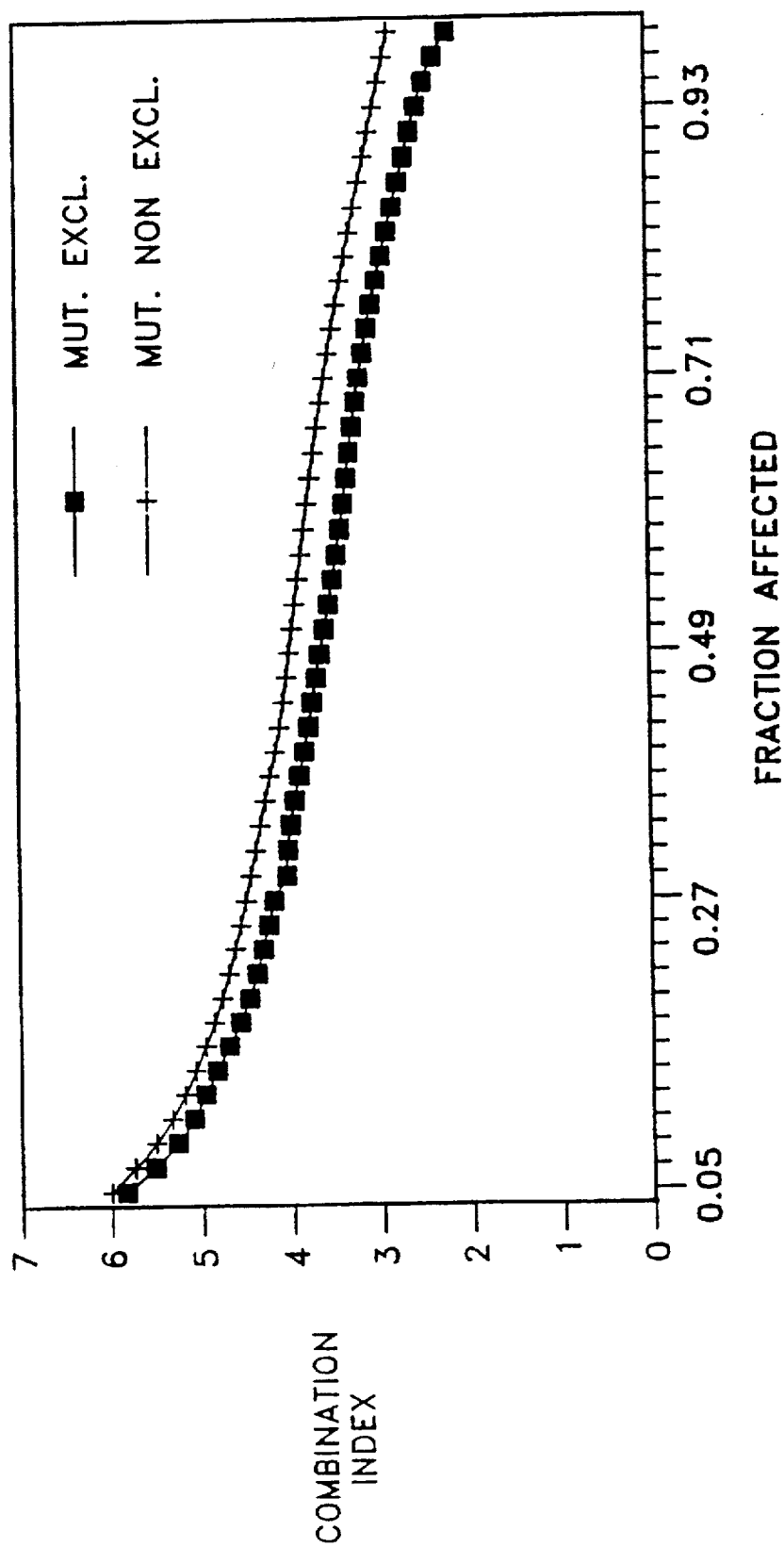

Thus, we have found that suramin is synergistic with vinblastine against both human prostate and breast cancer cells in vitro. In addition, we observed that suramin and estramustine were also synergistic in MCF-7 cells and additive in activity against PC-3 cells. It is conceivable that nonoverlapping toxicities of both estramustine and suramin may translate into clear synergy when this combination is given in the clinical setting.

In contrast, suramin in combination with microtubule inhibitors such as taxol, navelbine, or colchicine proved to be antagonistic. Similarly, combinations of suramin with polyamine inhibitors were antagonistic, whereas suramin with carboplatinum was merely additive.

The foregoing data establish an unexpectedly favorable interaction between suramin and either a vinca alkaloid antitumor agent or estramustine. Accordingly, this invention provides a method of treating prostate cancer and breast cancer comprising administering suramin in a regimen together with either a vinca alkaloid antitumor agent or estramustine. The combination generally will include each active ingredient packaged separately, thereby avoiding any interaction between the agents prior to administration. If desired, the individually packaged drugs can be placed in a single carton, thereby providing convenience to the attending physician or medical attendant.

We claim:

1. A synergistic combination of antineoplastic agents comprising an antitumor amount of suramin and an antitumor amount of estramustine.

2. A combination of claim 1 employing suramin as the hexasodium salt.

3. A combination of claim 2 employing estramustine or a pharmaceutically acceptable salt.

4. A combination of claim 3 employing estramustine phosphate sodium.

5. A method of treating cancer comprising administering to an animal in need of treatment an antitumor amount of a combination of claim 1.

6. A method of claim 5 wherein the cancer treated is prostate cancer.

7. A method of claim 6 employing suramin hexasodium in combination with estramustine phosphate sodium.

8. A method of claim 5 wherein the cancer treated is breast cancer.

9. A method of claim 8 employing suramin hexasodium in combination with estramustine phosphate sodium.

* * * * *